US012702521B2

(12) United States Patent
Morgan et al.

(10) Patent No.: US 12,702,521 B2
(45) Date of Patent: Aug. 11, 2026

(54) APPARATUS AND METHODS FOR SURGICAL LIGHTING

(71) Applicants: Dignity Health, San Francisco, CA (US); The Texas A&M University System, College Station, TX (US)

(72) Inventors: Clinton Morgan, San Francisco, CA (US); Peter Nakaji, San Francisco, CA (US); Sung Il Park, College Station, TX (US)

(73) Assignee: Dignity Health, San Francisco, CA (US)

(*) Notice: Subject to any disclaimer, the term of this patent is extended or adjusted under 35 U.S.C. 154(b) by 0 days.

(21) Appl. No.: 18/965,784

(22) Filed: Dec. 2, 2024

(65) Prior Publication Data

US 2025/0090263 A1 Mar. 20, 2025

Related U.S. Application Data

(63) Continuation of application No. 18/299,959, filed on Apr. 13, 2023, now Pat. No. 12,193,887, which is a (Continued)

(51) Int. Cl.
*A61B 90/30* (2016.01)
*A61B 17/00* (2006.01)
(Continued)

(52) U.S. Cl.
CPC ................ *A61B 90/30* (2016.02); *F21S 2/00* (2013.01); *A61B 2017/00734* (2013.01);
(Continued)

(58) Field of Classification Search
CPC .......... A61B 90/30; A61B 2017/00734; A61B 2017/00946; A61B 2090/3966;
(Continued)

(56) References Cited

U.S. PATENT DOCUMENTS

| | | | |
|---|---|---|---|
| 4,889,107 | A | 12/1989 | Kaufman |
| 5,733,252 | A | 3/1998 | Yoon |

(Continued)

FOREIGN PATENT DOCUMENTS

| | | | |
|---|---|---|---|
| EP | 2314247 | A1 | 4/2011 |
| WO | 2013/019904 | A2 | 2/2013 |
| WO | 2017/004531 | A1 | 1/2017 |

OTHER PUBLICATIONS

Patent Cooperation Treaty, International Search Report and Written Opinion, International Application No. PCT/US2018/020495, May 11, 2018, 9 pages.

(Continued)

*Primary Examiner* — Tsion Tumebo
(74) *Attorney, Agent, or Firm* — Polsinelli PC

(57) ABSTRACT

An apparatus for surgical lighting is disclosed. The apparatus includes a light emitting element formed with a light source encapsulated within an outer layer. The outer layer includes a biocompatible material. A power supply is coupled to the light source. The apparatus includes an actuating mechanism that controls power from the power supply to the light source to emit light along a surgical area. The light emitting element provides enhanced illumination and other surgical advantages.

16 Claims, 9 Drawing Sheets

Related U.S. Application Data continuation of application No. 16/490,531, filed as application No. PCT/US2018/020495 on Mar. 1, 2018, now Pat. No. 11,648,079.

(60) Provisional application No. 62/465,248, filed on Mar. 1, 2017.

(51) Int. Cl.

| | |
|---|---|
| ***A61B 90/00*** | (2016.01) |
| ***F21S 2/00*** | (2016.01) |
| ***F21W 131/20*** | (2006.01) |
| ***F21Y 115/10*** | (2016.01) |

(52) U.S. Cl.
CPC ............... *A61B 2017/00946* (2013.01); *A61B 2090/3966* (2016.02); *F21W 2131/20* (2013.01); *F21Y 2115/10* (2016.08)

(58) Field of Classification Search
CPC .... A61B 2090/309; A61B 2017/00212; A61B 17/00234; F21S 2/00; F21W 2131/20; F21Y 2115/10; F21V 23/045
See application file for complete search history.

(56) References Cited

U.S. PATENT DOCUMENTS

| | | | | |
|---|---|---|---|---|
| 7,234,853 | B2 | 6/2007 | Givoletti | |
| 7,611,256 | B2 | 11/2009 | Becker et al. | |
| 10,596,388 | B2 | 3/2020 | Hsieh et al. | |
| 11,648,079 | B2 | 5/2023 | Morgan et al. | |
| 11,826,495 | B2 * | 11/2023 | Nguyen .................. | A61L 31/10 |
| 2003/0004473 | A1 | 1/2003 | Bonadio et al. | |
| 2005/0107870 | A1 | 5/2005 | Wang et al. | |
| 2006/0195165 | A1 | 8/2006 | Gertner et al. | |
| 2006/0291195 | A1 | 12/2006 | Horrell et al. | |
| 2007/0060795 | A1 | 3/2007 | Vayser et al. | |
| 2007/0233208 | A1 | 10/2007 | Kurtz et al. | |
| 2007/0239232 | A1 | 10/2007 | Kurtz et al. | |
| 2008/0033519 | A1 | 2/2008 | Burwell et al. | |
| 2008/0132933 | A1 | 6/2008 | Gerber | |
| 2008/0269846 | A1 | 10/2008 | Burwell et al. | |
| 2009/0226643 | A1 | 9/2009 | Shih | |
| 2010/0081895 | A1 | 4/2010 | Zand | |
| 2010/0087713 | A1 | 4/2010 | Eliash | |
| 2010/0145415 | A1 | 6/2010 | Dahm et al. | |
| 2011/0034912 | A1 | 2/2011 | de Graff et al. | |
| 2011/0230747 | A1 * | 9/2011 | Rogers ..................... | A61B 5/05<br>600/377 |
| 2012/0046667 | A1 | 2/2012 | Cherry et al. | |
| 2012/0101342 | A1 | 4/2012 | Duffy et al. | |
| 2013/0046172 | A1 | 2/2013 | Waitzman et al. | |
| 2013/0103024 | A1 | 4/2013 | Monson et al. | |
| 2013/0116612 | A1 | 5/2013 | Stephan | |
| 2015/0032070 | A1 | 1/2015 | Colby | |
| 2016/0317005 | A1 | 11/2016 | Dunlop | |
| 2017/0020402 | A1 * | 1/2017 | Rogers ................. | A61B 5/0031 |
| 2017/0128015 | A1 | 5/2017 | Rogers et al. | |
| 2017/0239396 | A1 | 8/2017 | D'Agostino et al. | |
| 2018/0228483 | A1 | 8/2018 | Duggal et al. | |
| 2020/0121411 | A1 | 4/2020 | Morgan et al. | |
| 2023/0248465 | A1 | 8/2023 | Morgan et al. | |

OTHER PUBLICATIONS

Japan Patent Office, Final Office Action, Application No. 2019-547699, mailing date Nov. 1, 2022 4 pages.
European Patent Office, European Search Report, Application No. 18760524.1, Nov. 16, 2020.
European Patent Office, Communication Pursuant to Article 94(3) EPC, Application No. 18760524.1, Aug. 18, 2023, 8 pages.

* cited by examiner 900
911
902
LED LED LED LED
1M
470K
470K
D S G D
NMOS PMOS NMOS
G S D G S
10K
1uF
470K
SW
914
916
906
Battery

APPARATUS AND METHODS FOR SURGICAL LIGHTING

CROSS REFERENCE TO RELATED APPLICATIONS

This is a continuation application that claims benefit from U.S. application Ser. No. 18/299,959 filed Apr. 13, 2023, which claims benefit from U.S. 371 National patent application Ser. No. 16/490,531 filed Aug. 31, 2019, which claims the benefit of International Application No. PCT/US18/20495, filed Mar. 1, 2018, which claims benefit from U.S. provisional application Ser. No. 62/465,248 filed on Mar. 1, 2017, which are incorporated by reference in its entirety.

FIELD

The present disclosure generally relates to a surgical lighting apparatus and related methods for surgical lighting that include at least a light emitting element defining a light source and an outer layer for illuminating areas during a surgical procedure.

BACKGROUND

Conventional surgical lighting materials generally provide illumination from an external source such as a dissecting microscope, which may be oriented into a cavity or mounted on a surgical instrument. Surgical instruments with lighting implements include retractors, endoscopes, orthoscopic tools, suction tubes, and the like. However, such conventional implements and instruments do not provide adequate lighting during various surgical procedures. For example, deep surgical approaches, such as during aneurysm surgery, are far more dangerous under low-light conditions where the only light source consists of an external light source located outside the body. Visualization in this example is limited, and risk of injury is substantially increased. As another example, various neurological procedures require deep dissection, yet, the only light source may consist of a microscope light oriented outside the patient.

More general surgical procedures may be susceptible to low-light conditions as well. Laparoscopic surgery also involves low-light conditions where the only source of light in the abdomen is a single point source of light from an endoscope. Such limitations in lighting may limit visibility and in some cases may complicate the given procedure.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
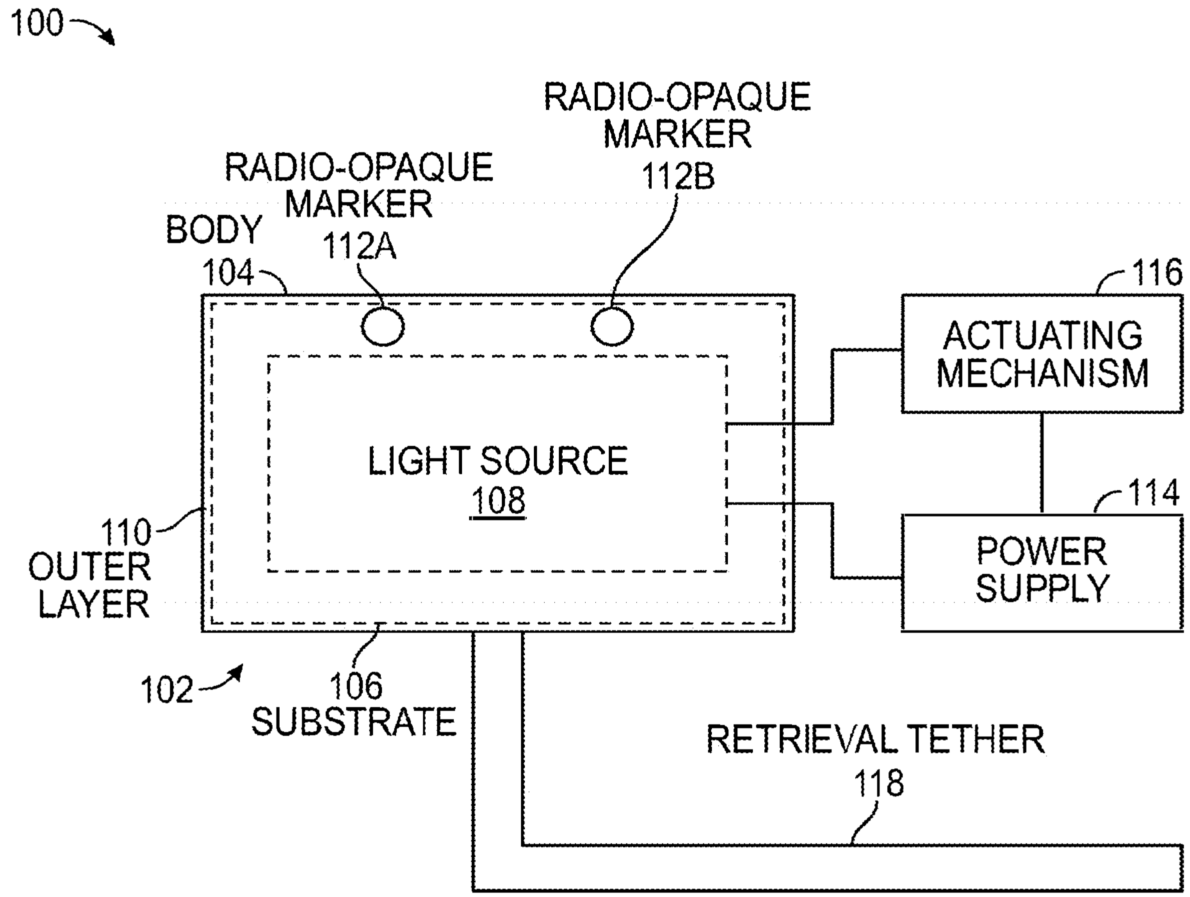
FIG. 1 is a simplified block diagram of an apparatus for surgical lighting, according to aspects of the present disclosure.

The present disclosure relates to surgical lighting equipment, and more particularly to an apparatus and methods for surgical lighting including a light emitting element. The light emitting element defines a light source oriented along a substrate, an outer layer for encapsulating or enclosing the light source, a power supply for powering the light source, and an actuation mechanism for controlling power from the power supply to the light source to illuminate a surgical area. In some embodiments, the outer layer is biocompatible, and both the substrate and outer layer are malleable such that the light emitting element is suitable for various surgical applications. Referring to the drawings, embodiments of an apparatus for surgical lighting are illustrated and generally indicated as 100, 200, 300, 400, and 500 in FIGS. 1-14.

Referring to FIG. 1, one embodiment of an apparatus for surgical lighting, designated 100, includes a light emitting element 102. The light emitting element 102 may define a body 104, which may be formed with dimensions ranging from 0.2 centimeters×0.2 centimeters to 4×4 centimeters or larger. In some embodiments, the body 104 may be formed with dimensions on a micrometer or nanometer scale, or may be generally microscopic (e.g., a predetermined number of microns in diameter) as desired for different applications. In one specific embodiment, the body 104 may be generally 6 mm in length. In some embodiments, the body 104 may generally define a three-dimensional general polygonal or rectangular-shape as shown, but may also take the form of other shapes more suitable for various surgical applications including specific lighting functions, as described herein.

In some embodiments, the body 104 may be multilayered as indicated. Specifically, the body 104 of the light emitting element 102 may define a substrate 106 oriented in a generally central position along the body 104. In some embodiments, the substrate 106 may include a generally planar member comprised of polyimide film or other flexible substrate material, with a plurality of copper or other conductive lines (not shown) formed along a surface of the polyimide film. The copper lines may be formed in a predefined pattern such that the substrate 106 is configured as a flexible printed circuit board (PCB), and the substrate 106 may define various electrical components (resistors, capacitors, switches, etc., not shown in FIG. 1) to accommodate the lighting functions as further described herein.

The body 104 may further define a light source 108 mounted to or otherwise arranged along the substrate 106, with the light source 108 being in electrical communication with the electrical components (not shown in FIG. 1) of the substrate 106. The light source 108 may include one or more of a light emitting diode (LED), LED tape, a miniature halogen bulb, an electrodeless lamp, a low/high pressure sodium light, a fluorescent lamp, a metal halide lamp, a sulfur lamp, an incandescent bulb, a discharge lamp, an arc lamp, a gas-discharge lamp, and the like. In some embodiments, the light source 108 defines a generally centrally positioned lighted layer of the body 104. The light source 108 may take the form of various configurations for providing indwelling lighting to a surgical field. In one aspect, the light source 108 provides diffuse lighting to a surgical corridor that may be naturally dark or inadequately lit, for an improved surgical field of vision.

The body 104 may further define an outer layer 110 oriented around the light source 108 and the substrate 106. In this manner, the outer layer 110 encapsulates the light source 108 and the substrate 106 such that the light source 108 and substrate 106 are at least partially or fully enclosed within the outer layer 110 to protect the light source 108 from external factors such as bodily tissue or fluids. The outer layer 110 may include one or more layers, or additional layers, such as non-absorptive fibers woven near their borders to form a uniform surface around the substrate 106 and light source 108 whereby upon implementation of the outer layer 110 the substrate 106 and light source 108 may be positioned along a generally central position within the body 104. In some embodiments, the outer layer 110 includes polydimethylsiloxane (PDMS), and/or may include plastics, acrylics, parylene coatings, sponge material, and/or silicone polymers. In some embodiments, the outer layer 110 may be non-absorbent (or absorbent), fluid-resistant, flexible, insulating, and biocompatible such that the outer layer 110 is suitable for various surgical and medical applications and may be suitable for use with bodily tissue during a surgical procedure. The outer layer 110 may be woven about the substrate 106 and light source 108, or formed by deposition or other like methods. In some embodiments, the outer layer 110 of the light emitting element 102 may be formed using or more surgical patties (not shown) such that the light emitting element 102 may include sponge or cotton material. For example, the light source 108 may be positioned within a surgical patty (not shown). In these embodiments, the outer layer 110 may further include a disposable textile pad suitable for placement on or around tissue for providing fluid management or other surgical functions, as further described herein. Embodiments of the subject light emitting element 102 may be used in neurosurgery and positioned along surgical cavities to enhance illumination and also to protect normal, healthy nervous system tissue in a non-absorptive fashion during complex surgical dissections.

In some embodiments, the outer layer 110 may also include malleable memory-retaining materials such that the outer layer 110 (and the body 104 generally) of the light emitting element 102 is deformable or may be morphed to predetermined shape configurations and temporarily retain such configurations during deployment. Such flexibility of the outer layer 110 may accommodate the light emitting element 102 to be deformed to fit into difficult, narrow, or uneven surgical fields, and may allow the light emitting element 102 to be deformed to shape different configurations that are suitable for e.g., providing a barrier to fluids along a surgical area. In addition, the light emitting element 102 may further be prepackaged in a compact design, allowing deployment of the light emitting element 102 with a laparoscopic, cystoscopic, or hysteroscopic port for general surgery, urologic surgery, or gynecological surgery applications. As one specific example, the light emitting element 102 may be packaged in a folded configuration suitable for deployment through e.g., a laparoscopic port (not shown) within the abdominal or pelvic cavity. During deployment, the outer layer 110 further protects the light emitting element 102 from mechanical forces or stress exerted during movement or manipulation of the light emitting element 102. For example, the outer layer 110 is suitable to insulate and protect the light source 108 from mechanical shear created by e.g., forceps or other surgical tools that may be used to grasp, deform, and/or move the light emitting element 102 along a surgical area. In one embodiment, the outer layer 110 may include one or more windows which may be aligned over the light source 108 to increase illumination.

In some embodiments, the light emitting element 102 may further include one or more radio-opaque markers 112 or indicators, designated radio-opaque markers 112A and 112B, located along the body 104 or anywhere along, on, or within the apparatus 100. The radio-opaque markers 112 may be positioned anywhere along the body 104, such as the outer layer 110 and/or surfaces of the substrate 106, as desired. The radio-opaque markers 112 allow a surgeon to track and retrieve the light emitting element 102 from a surgical area using X-ray imaging (not shown). The radio-opaque markers 112 may be defined at discrete points along the body 104 as shown, or may be defined along a tape-like member or layer applied along the body 104. In one aspect, the radio-opaque markers 112 may be useful to reduce the risk of misplacing the light emitting element 102 within a surgical corridor.

As further indicated in FIG. 1, the light source 108 of the light emitting element 102 may be electrically coupled (wired or wirelessly) to a power supply 114 and an actuating mechanism 116. The power supply 114 may take a variety of forms and may include e.g., a battery that is rechargeable or disposable. In some embodiments, the power supply 114 may integrated within or positioned along the light emitting element 102. Alternatively, the power supply 114 may be oriented external to the light emitting element 102 and may be e.g., positioned outside of the surgical area during deployment of the light emitting element 102. The actuating mechanism 116 may include one or more switches, or like electromechanical devices, for controlling power from the power supply 114 to the light source 108. Possible switches of the actuating mechanism 116 may include pushbutton switches, rocker switches, slide switches, a rheostat, transformer, variable resistor, solid-state semiconductor dimmer or similar device for providing different levels of current to the light source 108, or the like. The power supply 114 may also be wirelessly triggered by the actuating mechanism 116. For example, in one specific embodiment, the actuating mechanism 116 may include a reed switch defined along the substrate 106 and configured to activate and/or deactivate power from the power supply 114 when a magnetic source is oriented proximate to the actuating mechanism 116. In another embodiment, the actuating mechanism 116 may include a receiver or antennae such that the actuating mechanism 116 may control the power from the power supply 114 to the light source 108 upon receiving one or more radio frequency signals. Further still, the light source 108 (and/or the power supply 114) may be powered by amplified radiofrequency (RF) energy or "wireless power" using a harvester and antennae (not shown), or may be powered by inductive coupling from a base station.

In some embodiments, the apparatus 100 may further include a retrieval tether 118, which may include a string, rope, or otherwise define a generally elongated member connected to the light emitting element 102. The retrieval tether 118 may be composed of a biocompatible material similar to the outer layer 110 and may allow a surgeon to physically retrieve the light emitting element 102 from a surgical area by pulling the retrieval tether 118 as needed. In addition, in other embodiments, the retrieval tether 118 may include an insulated electrical conduit to electrically couple the light source 108 to the power supply 114. More specifically, the retrieval tether 118 may include one more conductive layers, lines, or wires, surrounded by an insulating layer that electrically connects the power supply 114 and/or an external power source to the light source 108.

Figure 2A:
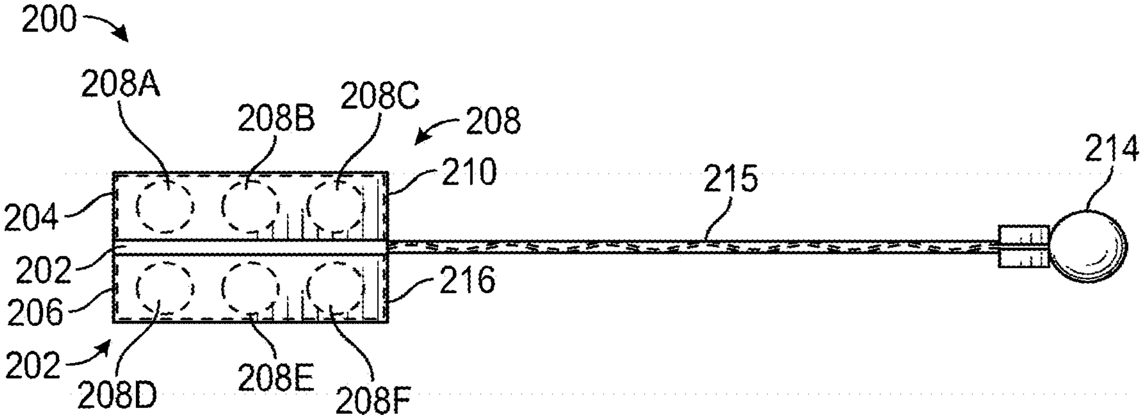
FIG. 2A is an illustration showing a top view of another embodiment of an apparatus for surgical lighting, according to aspects of the present disclosure.

Referring to FIG. 2A, another embodiment of an apparatus designated 200, and based on the general concept and functionality described in FIG. 1, may include a light emitting element 202 defining a body 204. The body 204 of the light emitting element 202 may define a substrate 206 oriented in a generally central position along the body 204. In some embodiments, the substrate 206 may include a generally planar member comprised of polyimide film or other flexible substrate material, with a plurality of plurality of copper or other conductive lines (not shown) formed along a surface of the polyimide film. The copper lines may be formed in a predefined pattern such that the substrate 206 is configured as a flexible PCB, and the substrate 206 may define various electrical components (resistors, capacitors, switches, etc., not shown) to accommodate the lighting functions as further described herein.

The body 204 may further define a light source 208, mounted to, coupled to, supported by, or otherwise oriented along the substrate 206. With the apparatus 200, the light source 208 may define a plurality of LEDs 208A-208F arranged along the substrate 206 as shown, and in electrical communication with the electrical components (not shown) of the substrate 206. In the example shown, the plurality of LEDs 208A-208F may be arranged in linear rows as indicated, but the present disclosure is not limited in this regard.

The body 204 may further define an outer layer 210 oriented around the plurality of LEDs 208A-208F and the substrate 206. In this manner, the outer layer 210 encloses the light source 208 and the substrate 206 at least partially or fully to protect the light source 208 from external factors such as bodily tissue or fluids. The outer layer 210 may include one or more layers that include e.g., non-absorptive fibers woven near their borders to form a uniform surface and enclose the substrate 206 and light source 208 within a generally central position along the body 204. In some embodiments, the outer layer 210 includes polydimethylsiloxane (PDMS), and/or may include plastics, acrylics, and/or silicone polymers. The outer layer 210 may be non-absorbent (or absorbent), fluid-resistant, flexible, insulating, and biocompatible such that the outer layer 210 is suitable for various surgical and medical applications. In some embodiments, the outer layer 210 may also include malleable memory-retaining materials such that the outer layer 210 (and the body 204 generally) of the light emitting element 202 is deformable or may be morphed to predetermined shape configurations and temporarily retain such configurations during deployment. In some embodiments, the outer layer 210 of the light emitting element 202 may be formed using or more surgical patties (not shown) such that the light emitting element 202 may include sponge or cotton material. For example, the light source 208 may be positioned within a surgical patty. In these embodiments, the outer layer 210 may further include a disposable textile pad suitable for placement on or around tissue for providing fluid management or other surgical functions, as further described herein. The subject light emitting element 202 may be used in neurosurgery and positioned along surgical cavities to enhance illumination and also to protect normal, healthy nervous system tissue in a non-absorptive fashion during complicated surgical dissections.

As further indicated in FIG. 2A, the light source 208 of the light emitting element 202 may be electrically coupled to a power supply 214 which may be implemented in the form of a battery external to the light emitting element 202 and may be a 3-9 volt battery although the present disclosure is not limited in this regard. In this manner, the power supply 214 may be positioned outside of the surgical area during deployment of the light emitting element 202. As further shown, the power supply 214 may be electrically coupled to the light source 208 by way of an electrical conduit 215. In some embodiments, the electrical conduit 215 may generally define one or more conductive lines surrounded by an insulating layer.

In some embodiments, the apparatus 200 includes an actuating mechanism 216 along the substrate 206 or proximate to the power supply 214 and electrically coupled to the power supply 214 and/or the light source 208. The actuating mechanism 216 may include one or more switches or like electromechanical devices for controlling power from the power supply 214 to the light source 208. Possible switches of the actuating mechanism 216 may include pushbutton switches, rocker switches, slide switches, a rheostat, transformer, variable resistor, solid-state semiconductor dimmer or similar device for providing different levels of current to the light source 208, or the like. The power supply 214 may also be wirelessly triggered by the actuating mechanism 216. For example, in one specific embodiment, the actuating mechanism 216 may include a reed switch configured to activate and/or deactivate power from the power supply 214 when a magnetic source is positioned proximate to the actuating mechanism 216. In another embodiment, the actuating mechanism 216 may include a receiver such that the actuating mechanism 216 is configured to control the power from the power supply 214 to the light source 208 upon receiving one or more radio frequencies. Further still, the light source 208 (and/or the power supply 214) may be powered by amplified radiofrequency (RF) energy or "wireless power," or may be powered by inductive coupling from a base station.

Figure 2B:
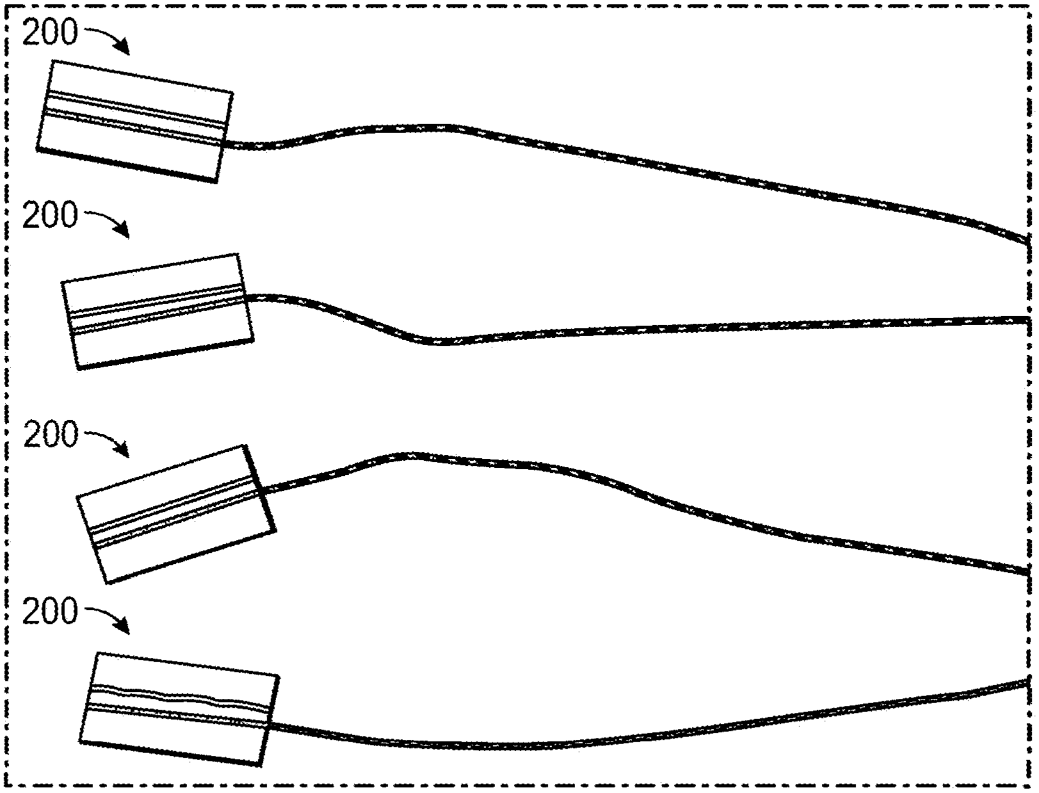
FIG. 2B is a top view of multiple examples of the embodiment of an apparatus for surgical lighting of FIG. 2A, according to aspects of the present disclosure.

The apparatus 200 may include additional aspects illustrated in FIG. 1. In some embodiments, for example, the apparatus 200 may further include one or more radio-opaque markers (not shown) arranged along the body 204 or the electrical conduit 215. In addition, a tether (not shown), similar to the retrieval tether 118 illustrated in FIG. 1, may be defined along the body 204. By way of example, FIG. 2B illustrates a set of the apparatuses 200 prior to deployment.

Figure 3:
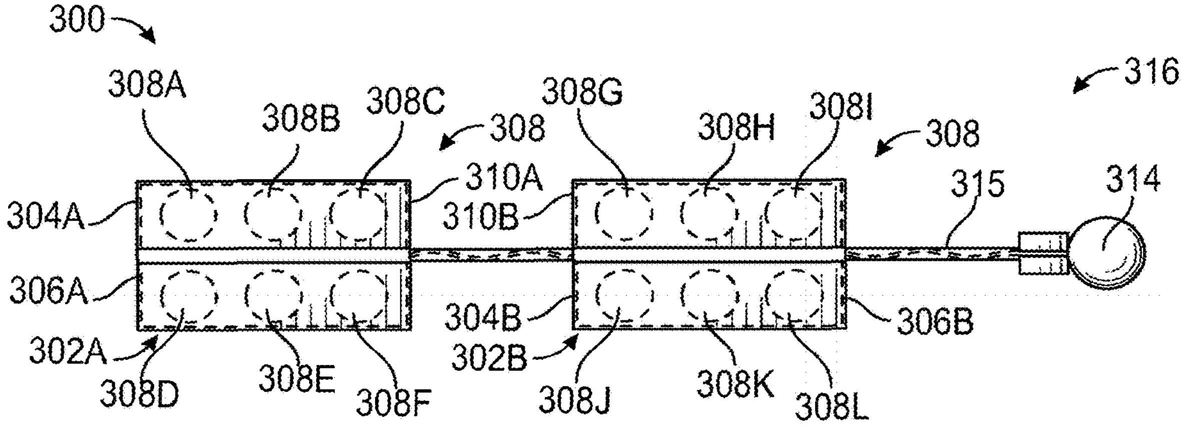
FIG. 3 is an illustration showing a top view of another embodiment of an apparatus for surgical lighting including multiple light emitting elements, according to aspects of the present disclosure.

Referring to FIG. 3, another embodiment of an apparatus designated 300, based on the general concept and functionality described in FIG. 1, may include a first light emitting element 302A defining a first body 304A, and a second light emitting element 302B defining a second body 304B such that the first light emitting element 302A and the second light emitting element 302B are oriented in a chain-like configuration. The first body 304A of the first light emitting element 302A may define a first substrate 306A oriented in a generally central position along the first body 304A. Similarly, the second body 304B of the second light emitting element 302B may define a second substrate 306B oriented in a generally central position along the second body 304B. In some embodiments, the substrates 306A and 306B may each define a generally planar member comprised of polyimide film or other flexible substrate material, with a plurality of plurality of copper or other conductive lines (not shown) formed along a surface of the polyimide film. The copper lines may be formed in a predefined pattern such that the substrates 306A and 306B are configured as flexible PCBs. In addition, the substrates 306A and 306B may define various electrical components (resistors, capacitors, switches, etc., not shown) to accommodate the lighting functions as further described herein.

The apparatus 300 may define a light source 308, represented as a plurality of LEDs 308A-308F mounted to or otherwise oriented along the first substrate 306A and a plurality of LEDs 308G-308L mounted to or otherwise oriented along the second substrate 306B. In the example shown, the plurality of LEDs 308A-308F and the plurality of LEDs 308G-308L may be arranged in linear rows as indicated, but the present disclosure is not limited in this regard.

The first body 304A may further define an outer layer 310A positioned around the plurality of LEDs 308A-308F and the first substrate 306A. In this manner, the outer layer 310A encloses both the plurality of LEDs 308A-308F and the first substrate 306A at least partially or fully to protect the plurality of LEDs 308A-308F from external factors such as bodily tissue or fluids. In addition, the outer layer 310A may include one or more layers that include e.g., non-absorptive fibers woven near its borders to form a uniform surface and enclose the first substrate 306A and the plurality of LEDs 308A-308F within a generally middle position along the first body 304A. In some embodiments, the outer layer 310A includes PDMS, and/or may include plastics, acrylics, and/or silicone polymers. The outer layer 310A may be non-absorbent (or absorbent), fluid-resistant, flexible, insulating, and biocompatible such that the outer layer 310A is suitable for various surgical and medical applications. In some embodiments, the outer layer 310A may also include a malleable memory-retaining material such that the outer layer 310A (and the first body 304A generally) of the first light emitting element 302A is deformable or may be morphed to predetermined shape configurations and temporarily retain such configurations during deployment.

In addition, the second body 304B may further define an outer layer 310B positioned around the plurality of LEDs 308G-308L and the second substrate 306B. In this manner, the outer layer 310B encloses both the plurality of LEDs 308G-308L and the second substrate 306B at least partially or fully to protect the plurality of LEDs 308G-308L from external factors such as bodily tissue or fluids. The outer layer 310B may include one or more layers that include e.g., non-absorptive fibers woven near their borders to form a uniform surface and enclose the second substrate 306B and the plurality of LEDs 308G-308L within a generally middle position along the second body 304B. In some embodiments, the outer layer 310B includes PDMS, and/or may include plastics, acrylics, and/or silicone polymers. The outer layer 310B may be non-absorbent, fluid-resistant, flexible, insulating, and biocompatible such that the outer layer 310B is suitable for various surgical and medical applications. In some embodiments, the outer layer 310B may also include a malleable memory-retaining material such that the outer layer 310B (and the second body 304B generally) of the second light emitting element 302B is deformable or may be morphed to predetermined shape configurations and temporarily maintain such configurations during deployment. In some embodiments, the outer layer 310A or the outer layer 310B may be formed using or more surgical patties (not shown) such that the light emitting elements 302A and 302B may include sponge or cotton material. For example, each of the light emitting elements 302A and 302B may be positioned within a surgical patty (not shown). In these embodiments, the outer layer 310A or the outer layer 310B may further include a disposable textile pad suitable for placement on or around tissue for providing fluid management or other surgical functions, as further described herein.

As further shown, the light source 308 of the apparatus 300 may be electrically coupled to a power supply 314 which may be implemented in the form of a battery external to the first light emitting element 302A and the second light emitting element 302B and may be a 3-9 volt battery although the present disclosure is not limited in this regard. In this manner, the power supply 314 may be positioned outside of the surgical area during deployment of the first and second light emitting elements 302A and 302B. As further shown, the power supply 314 may be electrically coupled to the light source 308 by way of an electrical conduit 315. The electrical conduit 315 may generally define one or more conductive lines surrounded by an insulating layer. More specifically, the electrical conduit 315 may be electrically coupled along the first light emitting element 302A and the second light emitting element 302B to create the chain-like configuration and extend access to power from the power supply 314 and the second light emitting element 302B to the first light emitting element 302A. In other embodiments, the power supply 314 may be connected in parallel, rather than in series as shown. In some embodiments, the each of the first lighting element 302A and the second light emitting element 302B may be coupled to individual respective power supplies (not shown).

In some embodiments, the apparatus 300 includes one or more of an actuating mechanism 316 along the first substrate 306A and/or second substrate 306B or proximate to the power supply 314 and electrically coupled to the power supply 314 and/or the light source 308. The actuating mechanism 316 may include one or more switches or like electromechanical devices for controlling power from the power supply 314 to the light source 308. Possible switches of the actuating mechanism 316 may include pushbutton switches, rocker switches, slide switches, dimming devices including a transformer, variable resistor, or solid-state semiconductor dimmer, or the like. The power supply 314 may also be wirelessly triggered by the actuating mechanism 316. For example, in one specific embodiment, the actuating mechanism 316 may include a reed switch configured to activate and/or deactivate power from the power supply 314 when a magnetic source is oriented proximate to the actuating mechanism 316. In another embodiment, the actuating mechanism 316 may include a receiver such that the actuating mechanism 316 is configured to control the power from the power supply 314 to the light source 308 upon receiving one or more radio frequencies. Further still, the light source 308 (and/or the power supply 314) may be powered by amplified RF energy or "wireless power," or may be powered by inductive coupling from a base station.

The apparatus 300 may include additional aspects illustrated in FIG. 1. In some embodiments, for example, the apparatus 300 may further include one or more radio-opaque markers (not shown) arranged along the first light emitting element 302A, the second light emitting element 302B, or the electrical conduit 315. In addition, a tether (not shown), similar to the retrieval tether 118 illustrated in FIG. 1, may be defined along the apparatus 300.

Figure 4:
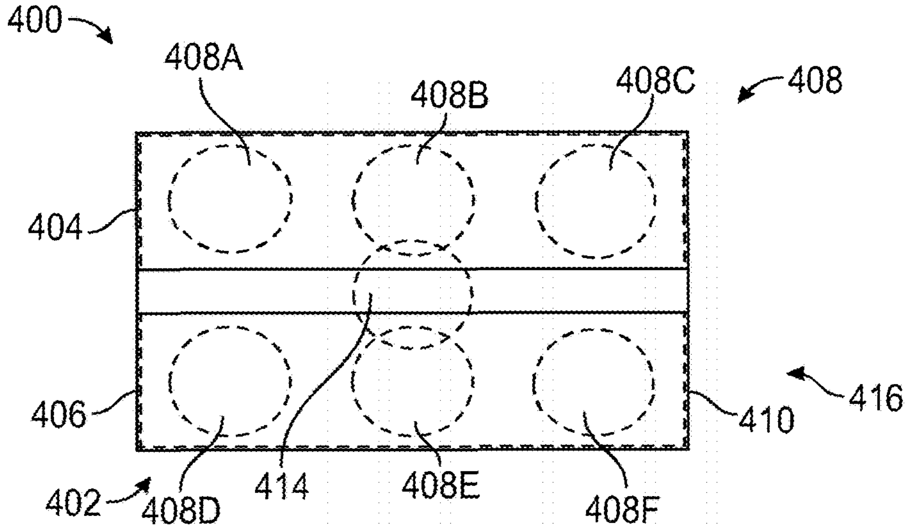
FIG. 4 is a top view of another embodiment of an apparatus for surgical lighting defining a discrete light emitting element with an embedded battery, according to aspects of the present disclosure.

Referring to FIG. 4, another embodiment of an apparatus designated 400, based on the general concept and functionality described in FIG. 1, may include a light emitting element 402 defining a body 404. The body 404 of the light emitting element 402 may define a substrate 406 oriented in a generally central position along the body 404. In some embodiments, the substrate 406 may define a generally planar member comprised of polyimide film or other flexible substrate material, with a plurality of plurality of copper or other conductive lines (not shown) formed along a surface of the polyimide film. The copper lines may be formed in a predefined pattern such that the substrate 406 is configured as a flexible PCB. In addition, the substrate 406 may define various electrical components (resistors, capacitors, switches, etc., not shown) to accommodate the lighting functions as further described herein.

The body 404 may further define a light source 408, mounted to or otherwise oriented along the substrate 406. With the apparatus 400, the light source 408 may include one or more LEDs, designated 408A-408F arranged along the substrate 406 as shown, and in electrical communication with the electrical components (not shown) of the substrate 406. In the example shown, the plurality of LEDs 408A-408F may be arranged in linear rows as indicated, but the present disclosure is not limited in this regard.

The body 404 may further define an outer layer 410 oriented around the plurality of LEDs 408A-408F and the substrate 406. In this manner, the outer layer 410 encapsulates the light source 408 and the substrate 406 at least partially or fully to protect the light source 408 from external factors such as bodily tissue or fluids. The outer layer 410 may include one or more layers that include e.g., non-absorptive fibers woven near their borders to form a uniform surface and enclose the substrate 406 and light source 408 within a generally middle position along the body 204. In some embodiments, the outer layer 410 includes PDMS, and/or may include plastics, acrylics, and/or silicone polymers. The outer layer 410 may be non-absorbent (or absorbent), fluid-resistant, flexible, insulating, and biocompatible such that the outer layer 410 is suitable for various surgical and medical applications. In some embodiments, the outer layer 410 may also include malleable memory-retaining materials such that the outer layer 410 (and the body 404 generally) of the light emitting element 402 is deformable or may be morphed to predetermined shape configurations and temporarily retain such configurations during deployment. In some embodiments, the outer layer 410 of the light emitting element 402 may be formed using or more surgical patties (not shown) such that the light emitting element 402 may include sponge or cotton material. For example, the light source 408 may be positioned within a surgical patty. In these embodiments, the outer layer 410 may further include a disposable textile pad suitable for placement on or around tissue for providing fluid management or other surgical functions, as further described herein. The subject light emitting element 402 may be used in neurosurgery and positioned along surgical cavities to enhance illumination and also to protect normal, healthy nervous system tissue in a non-absorptive fashion during complicated surgical dissections.

As further indicated, the light source 408 of the light emitting element 402 may be electrically coupled to a power supply 414 which may be implemented in the form of a 3-9 volt battery, although the present disclosure is not limited in this regard. In this embodiment of the apparatus 400, the power supply 414 may be positioned along the light emitting element 402, and may be integrated within the outer layer 410 and mounted to the substrate 406, for example. In this manner, the light emitting element 402 is generally discrete and wireless in its application.

In some embodiments, the apparatus 400 further includes an actuating mechanism 416 along the substrate 406 or proximate to the power supply 414 and electrically coupled to the power supply 414 and/or the light source 408. The actuating mechanism 416 may include one or more switches or like electromechanical devices for controlling power from the power supply 414 to the light source 408, which may be defined along the substrate 406. Possible switches of the actuating mechanism 416 may include pushbutton switches, rocker switches, slide switches, a rheostat, transformer, variable resistor, solid-state semiconductor dimmer, or similar device for providing different levels of current to the light source 408, or the like. The power supply 414 may also be wirelessly triggered by the actuating mechanism 416. For example, in one specific embodiment, the actuating mechanism 416 may include a reed switch configured to activate and/or deactivate power from the power supply 414 when a magnetic source is positioned proximate to the actuating mechanism 416. In another embodiment, the actuating mechanism 416 may include a receiver such that the actuating mechanism 416 is configured to control the power from the power supply 414 to the light source 408 upon receiving one or more radio frequencies. Further still, the light source 408 (and/or the power supply 414) may be powered by amplified RF energy or "wireless power," or may be powered by inductive coupling from a base station.

The apparatus 400 may include additional aspects illustrated in FIG. 1. In some embodiments, for example, the apparatus 400 may further include one or more radio-opaque markers (not shown) arranged along the body 404. In addition, a tether (not shown), similar to the retrieval tether 118 illustrated in FIG. 1, may be defined along the body 404.

Figure 5:
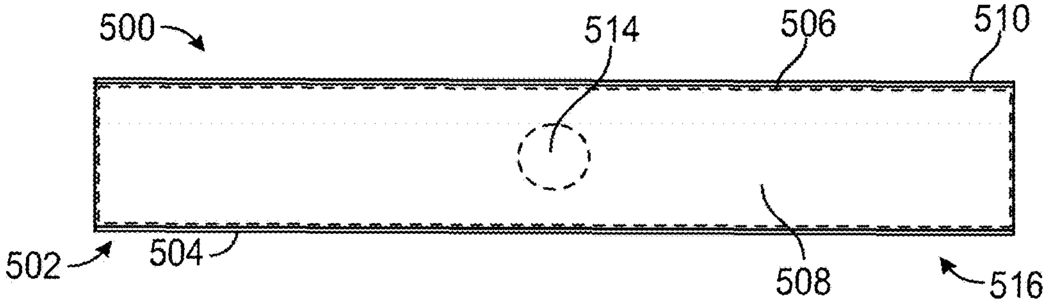
FIG. 5 is a top view of another embodiment of an apparatus for surgical lighting defining a light source that includes LED tape, according to aspects of the present disclosure.

Referring to FIG. 5, a fifth embodiment of an apparatus designated 500, based on the general concept and functionality described in FIG. 1, may include a light emitting element 502 defining a body 504. The body 504 of the light emitting element 502 may define a substrate 506 which is generally elongated and planar member comprised of polyimide film or other flexible substrate material, with a plurality of plurality of copper or other conductive lines (not shown) formed along a surface of the polyimide film. The copper lines may be formed in a predefined pattern such that the substrate 506 is configured as a flexible PCB, and the substrate 506 may define various electrical components (resistors, capacitors, switches, etc., not shown) to accommodate the lighting functions as further described herein.

The body 504 may further define a light source 508, mounted to or otherwise oriented along the substrate 506. With the apparatus 500, the light source 508 may define an LED strip light or LED tape in electrical communication with the electrical components (not shown) of the substrate 506. In some embodiments, the light source 508 may include surface mounted LEDs or surface mounted devices (SMD) LEDs which may include different shapes, sizes, and power levels, depending upon the application desired for the apparatus 500.

The body 504 may further define an outer layer 510 oriented around the light source 508 and the substrate 506. In this manner, the outer layer 510 encloses the light source 508 and the substrate 506 at least partially or fully to protect the light source 508 from external factors such as bodily tissue or fluids. The outer layer 510 may include one or more layers that include e.g., non-absorptive fibers woven near its borders to form a uniform surface and enclose the substrate 506 and light source 508 within a generally middle position along the body 504. In some embodiments, the outer layer 510 includes PDMS, and/or may include plastics, acrylics, and/or silicone polymers. The outer layer 510 may be non-absorbent (or absorbent), fluid-resistant, flexible, insulating, and biocompatible such that the outer layer 510 is suitable for various surgical and medical applications. In some embodiments, the outer layer 510 may also include malleable memory-retaining materials such that the outer layer 510 (and the body 504 generally) of the light emitting element 502 is deformable or may be morphed to predetermined shape configurations and temporarily retain such configurations during deployment. In some embodiments, the outer layer 510 of the light emitting element 502 may be formed using or more surgical patties (not shown) such that the light emitting element 502 may include sponge or cotton material. For example, the light source 508 may be positioned within a surgical patty (not shown). In these embodiments, the outer layer 510 may further include a disposable textile pad suitable for placement on or around tissue for providing fluid management or other surgical functions, as further described herein.

As further indicated, the light source 508 of the light emitting element 502 may be electrically coupled to a power supply 514 which may include a driver. In the embodiment shown, the power supply 514 is integrated within the outer layer 510 such that the light emitting element 502 is wireless, but the power supply 514 may also include a USB device, plug, or otherwise be wired in some form.

In some embodiments, the apparatus 500 further includes an actuating mechanism 516 positioned along the substrate 506 or proximate to the power supply 514 and electrically coupled to the power supply 514 and/or the light source 508. The actuating mechanism 516 may include one or more switches or like electromechanical devices for controlling power from the power supply 514 to the light source 508. Possible switches of the actuating mechanism 516 may include pushbutton switches, rocker switches, slide switches, a transformer, a variable resistor, a solid-state semiconductor dimmer, or the like. The power supply 514 may also be wirelessly triggered by the actuating mechanism 516. For example, in one specific embodiment, the actuating mechanism 516 may include a reed switch configured to activate and/or deactivate power from the power supply 514 when a magnetic source is positioned proximate to the actuating mechanism 516. In another embodiment, the actuating mechanism 516 may include a receiver such that the actuating mechanism 516 is configured to control the power from the power supply 514 to the light source 508 upon receiving one or more radio frequencies. Further still, the light source 508 (and/or the power supply 514) may be powered by amplified RF energy or "wireless power," or may be powered by inductive coupling from a base station.

The apparatus 500 may include additional aspects illustrated in FIG. 1. In some embodiments, for example, the apparatus 500 may further include one or more radio-opaque markers (not shown) arranged along the body 504. In addition, a tether (not shown), similar to the retrieval tether 118 illustrated in FIG. 1, may be defined along the body 504.

Other aspects and advantages of the various embodiments and light emitting elements 102, 202, 302, 402, 502 described in FIGS. 1-5 are contemplated. For example, any one of the described light emitting elements 102, 202, 302, 402, 502 may provide miniaturized surgical lighting, and may be on the millimeter or centimeter scale, as modern uLEDs may be as small as 25×25 micrometers, providing remarkable illumination to low-light surgical environments. Further, the light emitting elements 102, 202, 302, 402, 502 may sponge material, to reduce engagement to bodily tissue such that the light emitting elements 102, 202, 302, 402, 502 may be moveable along a surgical area unlike fixed lighting devices. In some embodiments, by implementing dimmer devices including rheostat dimmers, transformers, variable resistors, solid-state dimmers in the form of semiconductor devices, other devices for controlling the voltage waveform applied to the light sources 108, 208, 308, 408, and 508, the illumination provided by the light sources 108, 208, 308, 408, and 508 described may also be dimmable and adjustable as needed during deployment. In addition, the light emitting elements may be efficiently manufactured and entirely disposable.

Figure 6:
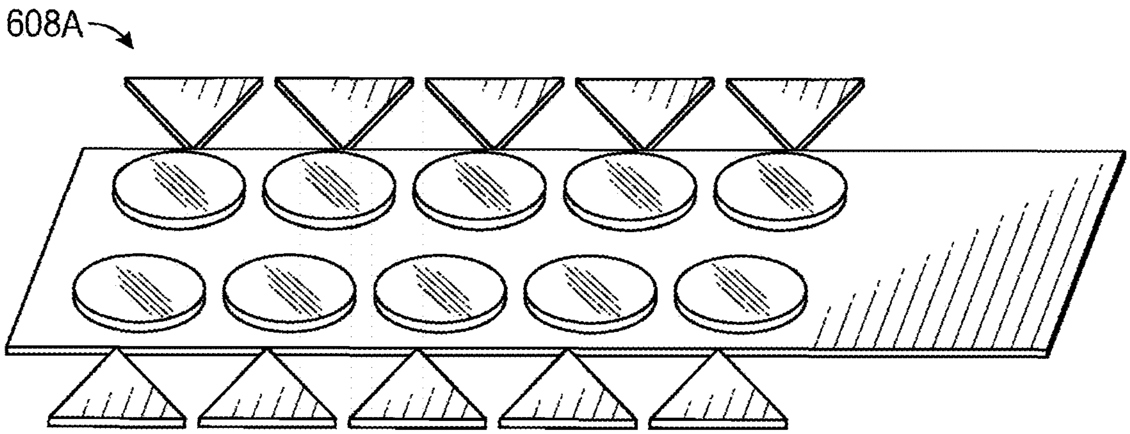
FIG. 6 illustrates a first configuration of a light source for use with any of the embodiments of the apparatus described herein, according to aspects of the present disclosure.

Referring to FIG. 6, one possible light source configuration 608A is shown which may be implemented with any one of the apparatuses 100, 200, 300, 400, 500 described herein. In this example, the light source configuration 608A defines a plurality of LEDs arranged in a columnar configuration or array, which may be ideal for providing columnar lighting. In other embodiments, the light source configuration 608A may include a plurality of LEDs arranged in a staggered configuration for providing more diffuse lighting, or a tight circular array for providing more focused lighting. The LEDs of the light source configuration 608A may further be arranged in offset, alternating, square, or diamond configurations.

Figure 7:
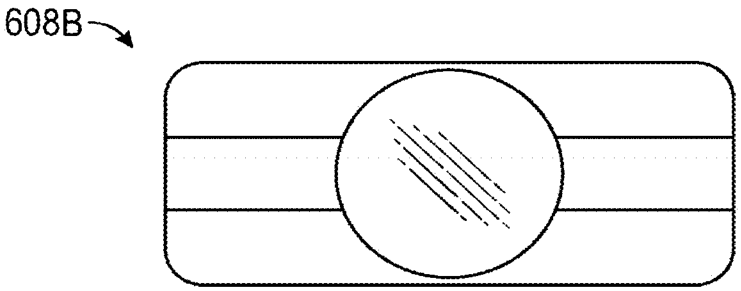
FIG. 7 illustrates a second configuration of a light source for use with any of the embodiments of the apparatus described herein, according to aspects of the present disclosure.

Referring to FIG. 7, another light source configuration 608B which may be implemented with any one of the apparatuses 100, 200, 300, 400, 500 described herein is shown which may include a sole LED or other light source arranged within a light emitting element similar to apparatus embodiments of FIGS. 1-5. Utilizing a single LED or light source may be suitable where it is desired that individual light emitting elements 102, 202, 302, 402, 502 be disposable or where such light emitting elements are mere micrometers in size. Each LED of FIGS. 6-7 may be on the order of tens of thousands of microns in diameter depending upon the illumination necessary and the size of a containing light emitting element.

Figure 8:
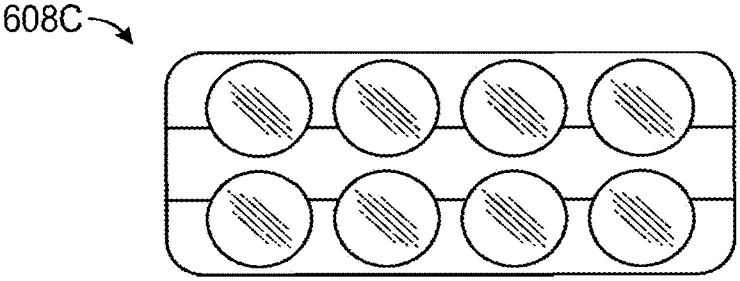
FIG. 8 illustrates a third configuration of a light source for use with any of the embodiments of the apparatus described herein, according to aspects of the present disclosure.
Figure 9:
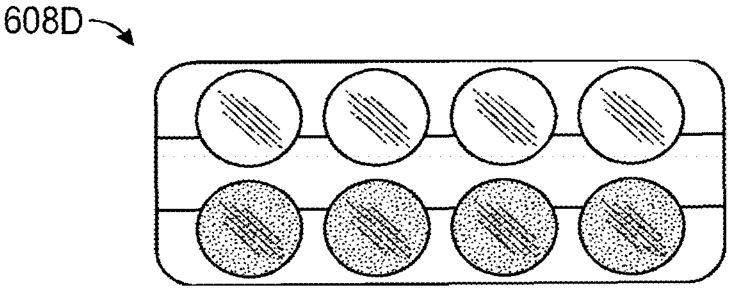
FIG. 9 illustrates a fourth configuration of a light source for use with any of the embodiments of the apparatus described herein, according to aspects of the present disclosure.

Referring to FIG. 8, another light source configuration 608C which may be implemented with any one of the apparatuses 100, 200, 300, 400, 500 described herein is shown. In this embodiment, the light source configuration 608C includes one or more LEDs or other light sources 108, 208, 308, 408, 508 that emit a uniform wavelength. In contrast, referring to FIG. 9, another embodiment of a light source configuration 608D which may be implemented with any one of the apparatuses 100, 200, 300, 400, 500 described herein includes one or more LEDs or other light sources 108, 208, 308, 408, 508 that emit varying wavelengths. FIGS. 8-9 illustrate that various types of LEDs may be implemented to provide different predefined surgical functions, e.g., illuminate a surgical area at specific wavelengths in order to achieve various benefits. In some embodiments, the wavelength of the light emitted from light sources 108, 208, 308, 408, 508 may be adjusted and depend upon the band gap energy of the predetermined semiconductor materials forming the p-n junction of a respective LED defined by the light sources 108, 208, 308, 408, 508. In other words, different semiconductor materials may be used to form LEDs representing the light sources 108, 208, 308, 408, 508 that may correspond to different desired wavelengths of light. Wavelengths may correspond to certain procedures that use dyes that are excited at a specific wavelength for e.g., tumor visualization and vascular flow assessment, wavelengths that provide antiseptic properties, wavelengths that provide better visual differentiation, reduce reflection, glare, or otherwise improve visual discrimination. With respect to a dye-based application, dyes are often inserted or ingested into the body, including vasculatures, neurological tissue, and ducts to better visualize cancerous tissue and arterial vasculature. These dyes contain molecules that when activated by light at a certain wavelength, emit light that is detectable either by sight or by various detection equipment. This allows a surgeon to detect the movement of fluids, uptake of molecules, blockages, breakages, etc.

In one specific possible implementation, blue spectrum lighting in the range of 375-440 nm could be utilized to visualize gliomas or tumors in general when patients are administered 5-aminolevulinic acid (5-ALA) to separate cancerous tissue from normal healthy tissue. Light in the wavelength near 494 nm could be used to excite fluorescein fluorophore for intra-operative separation of cancerous tissue from healthy tissue. Both 5-ALA and fluorescein have been widely tested in the United States and in Europe for resection of high-grade glioma from normal healthy tissue. Such an approach may allow alternative or supplementary excitatory light sources to assist the surgeon in visual identification of cancerous tissue. When the described light emitting elements 102, 202, 302, 402, 502 are deployed during surgery, identification of cancerous tissue could be greatly improved. For example, in deep head and neck surgery for cancers of the ear, nose, or throat, fluorescein excitation with surgical light emitting elements as described herein may be useful in narrow corridors to reach lesions of interest.

Another example of a specific implementation of the described light emitting elements 102, 202, 302, 402, 502 involves an LED emitting light in the range of 600-900 nm to excite indocyanine green (ICG), which can be used to visualize arterial blood flow when administered to a patient. Much like the applications with 5-ALA and fluorescein described herein, ICG may be excited by an additional supplemental light source in the form of the described light emitting element, allowing light excitation from sources beyond conventional lighted surgical tools.

Yet another example of a specific implementation involves emitting light in the ultraviolet-C range, which has been traditionally considered carcinogenic and cataractogenic. However, it has been recently shown that UV-C light does not penetrate human cell membranes; as such, it is highly bactericidal and viricidal without having a significant effect on human cells. UV-C light may be deployed from any one of the described light emitting elements 102, 202, 302, 402, 502 to decontaminate a surgical area from bacteria. Bacteria which are antibiotic resistant would also be susceptible to light emitted in the UV-C range.

Figure 10:
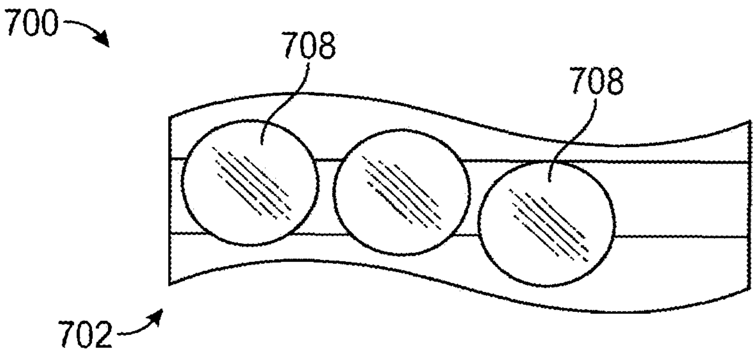
FIG. 10 illustrates a fifth configuration of a light source for use with any of the embodiments of the apparatus described herein, according to aspects of the present disclosure.

Referring to FIG. 10, another light source configuration 700 for a light emitting element 702 is shown with one or more light sources 708. This embodiment illustrates that the light emitting element 702 may take on different shape configurations, and that the light emitting element 702 may be malleable or bendable as needed. This embodiment further illustrates that the light source 708 may include a plurality of LEDs that are not necessarily arranged in linear rows.

Figure 11:
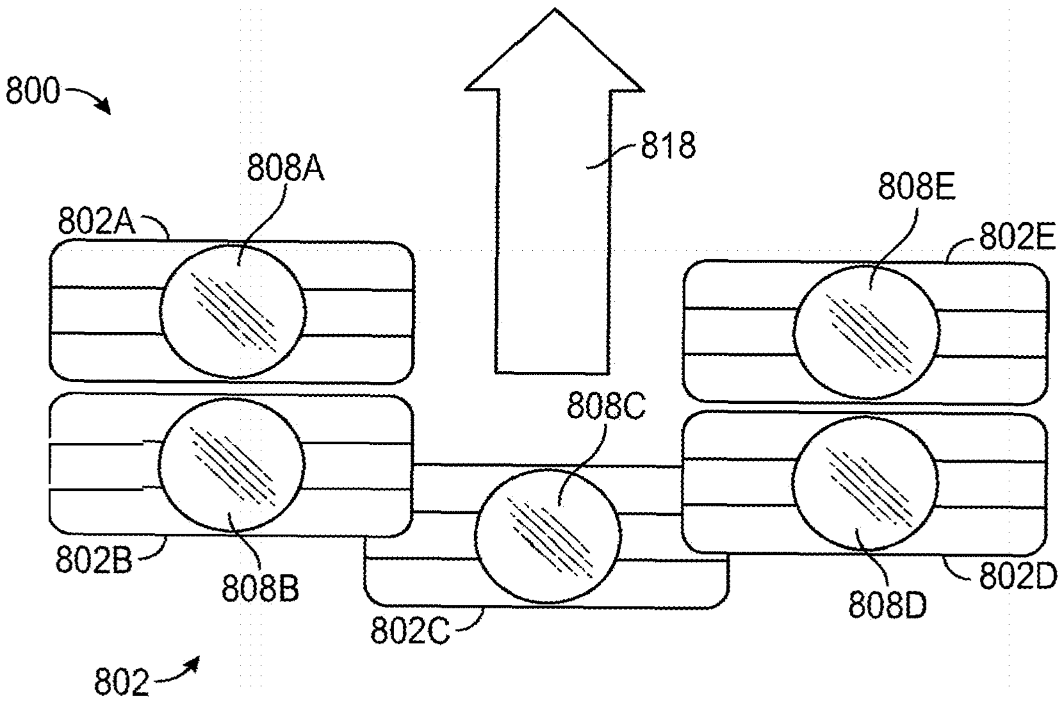
FIG. 11 illustrates an exemplary configuration for surgical deployment using a plurality of light emitting elements, according to aspects of the present disclosure.

Referring to FIG. 11, a configuration 800 for surgical deployment is illustrated that includes a plurality of light emitting elements 802A-802E, which may be similar to the other light emitting elements 102, 202, 302, 402, 502 described herein. In the configuration shown, the light emitting elements 802A-802E include, respectively, light sources 808A-808E. The configuration 800 illustrates that the plurality of light emitting elements 802A-802E may be arranged along a surgical area in this exemplary orientation shown in order to provide focused illumination 818 to a particular portion of a surgical area. As described herein, the lighted surgical light emitting elements 802A-802E may be arranged to provide columnated and directed light towards a point of focus. Light may emit from only one side of a light emitting element of the light emitting elements 802A-802E, or may emit from both sides. The flexible and convenient predetermined arrangement or manner in which the light emitting elements 802A-802E may be oriented (and shifted or moved) may accommodate focused light in a specific direction, and may also accommodate broader illumination as desired. In addition, the plurality of light emitting elements 802A-802E may be arranged as shown (or in other configurations) to provide a fluid-tight barrier around a surgical area.

Figure 12A:
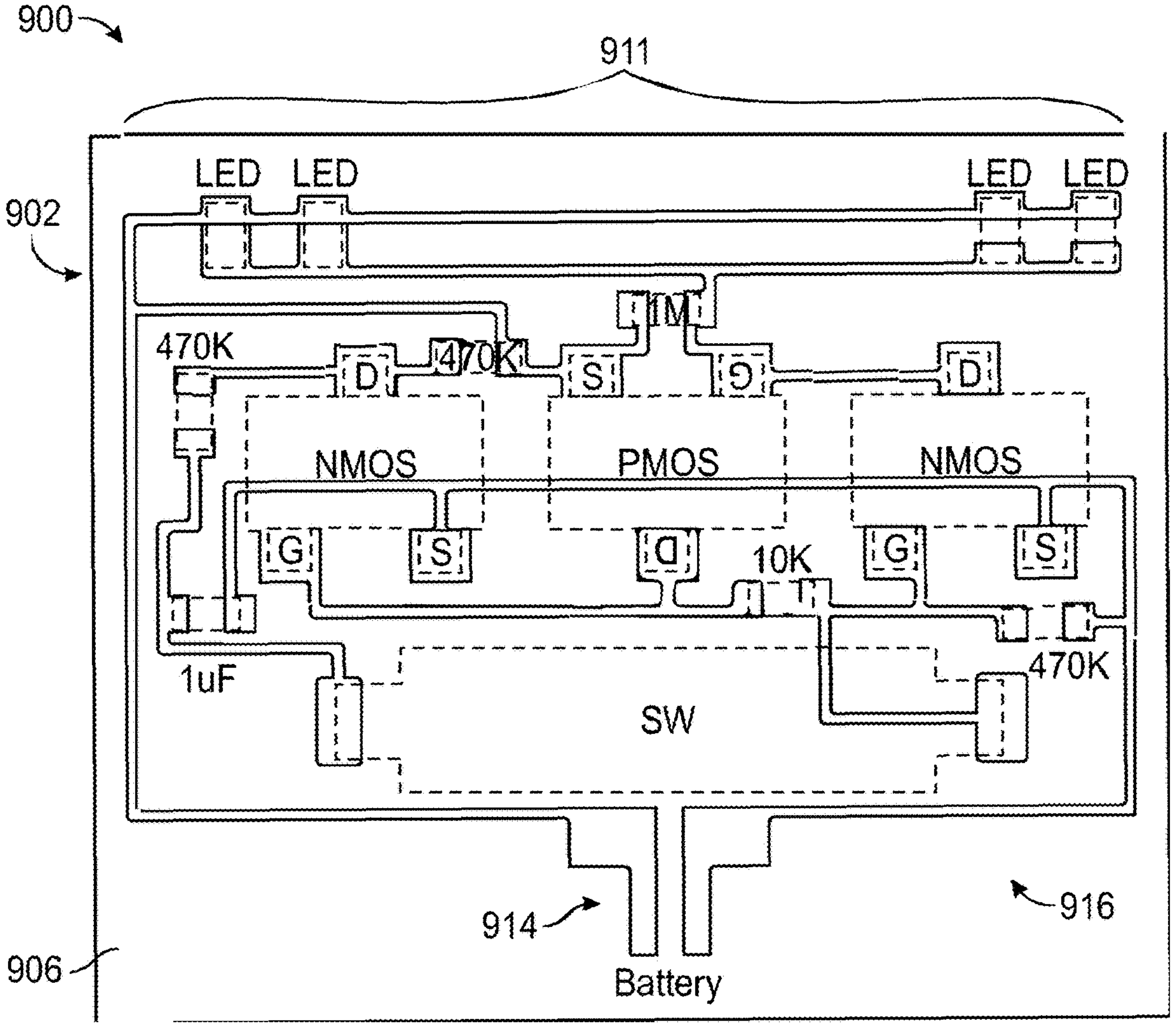
FIG. 12A is a mask layout for use with any of the embodiments of the apparatus described herein, according to aspects of the present disclosure.
Figure 12B:
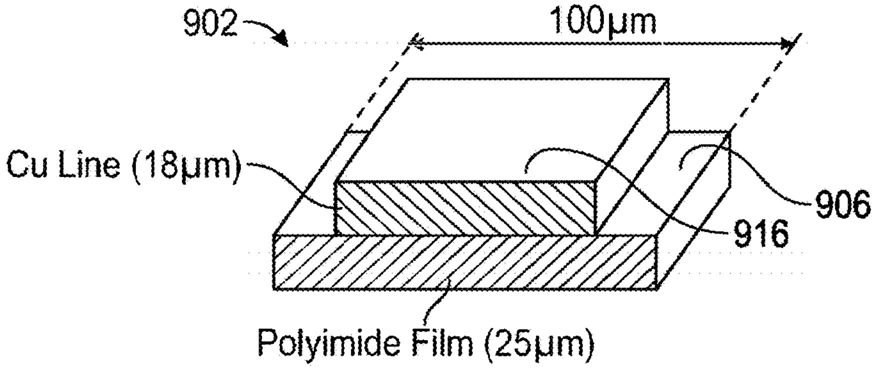
FIG. 12B is a cross sectional view of the mask layout of FIG. 12A, according to aspects of the present disclosure.

Referring to FIGS. 12A-12B and FIGS. 13A-13B, various possible electrical characteristics that may be implemented for any one of the embodiments of the light emitting elements 102, 202, 302, 402, 502, 702, 802 described are illustrated. Specifically, FIG. 12A illustrates an exemplary mask layout 900 for a light emitting element 902. The light emitting element 902 defines a substrate 906 that includes electrical components 911 such as a plurality of resistors, capacitors, a reed switch and one or more of an LED formed and/or mounted along the substrate 906. In one implementation, the electrical components 911 include a 470k resistor (0201)—3 each (ea); a 1M resistor (0201)—1 ea; a 10k resistor (0201)—1 ea; a 1 μF capacitor (0201)—1 ea; a reed switch—1 ea; a white LED (0201)—2 or 4 ea, a PMOS—1 ea; and an NMOS—2 ea. In some embodiments, the various electrical components 911 may be defined by conductive or copper (Cu) lines 916 formed along the substrate 906. The substrate 906 may further be coupled to a battery 914 as indicated. Referencing FIG. 12B, the Cu lines 916 formed along the substrate 906 may generally define a diameter of approximately 18 micrometers. As further indicated, in some embodiments, the polyimide film defining the substrate 906 may be 25 micrometers in diameter, and the light emitting element 902 may be approximately 100 micrometers in diameter. It should be understood that the mask layout 900 may be used with any of the light emitting elements 102, 202, 302, 402, 502, 702, 802, 902 described herein.

Figure 13A:
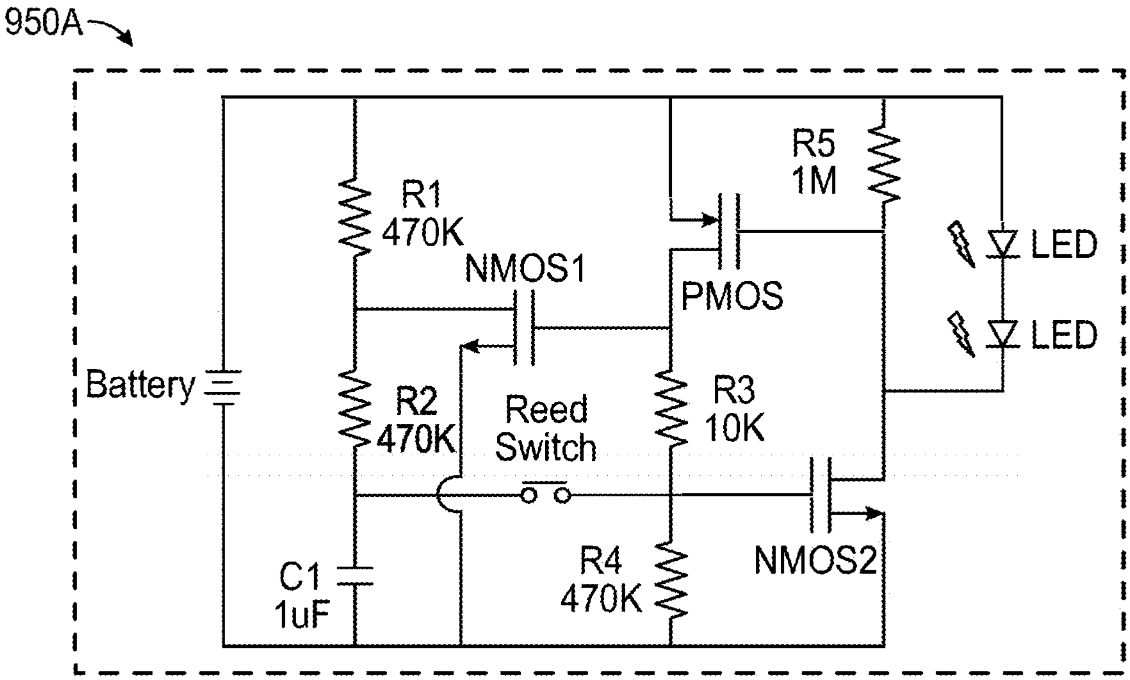
FIGS. 13A-13B are schematic circuit diagrams for use with any of the embodiments of the apparatus described herein, according to aspects of the present disclosure.
Figure 13B:
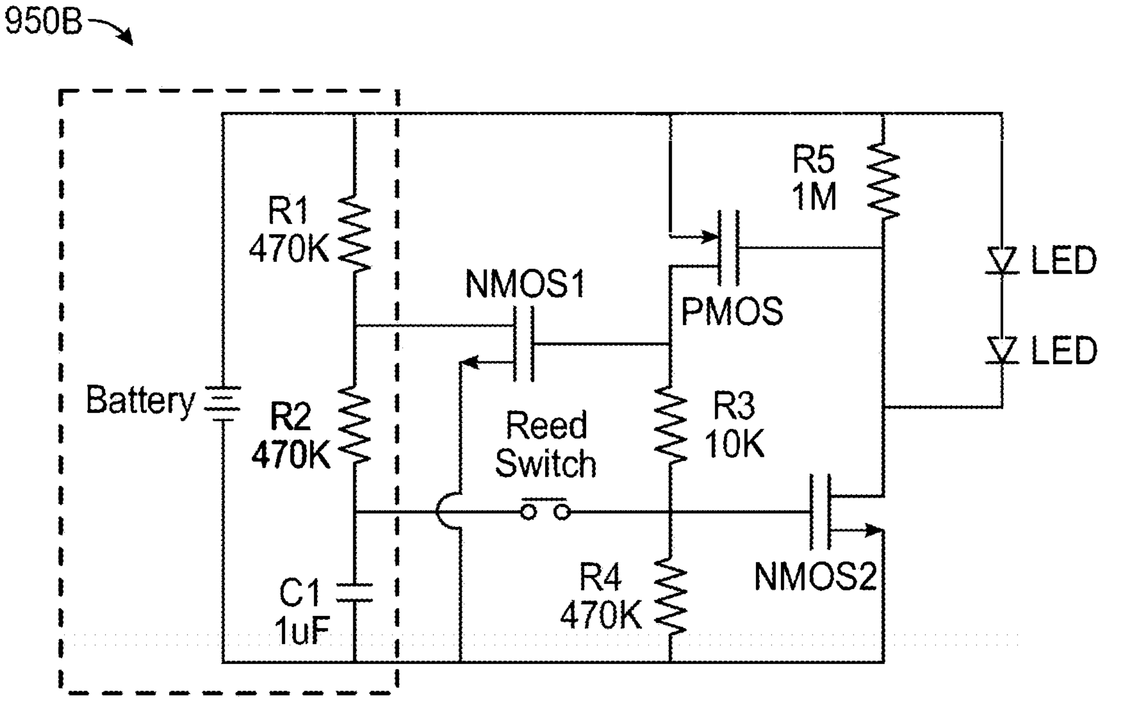

Referring to FIGS. 13A and 13B, schematic diagrams 950A and 950B are illustrated to indicate possible engagement of various electrical components when an LED or other light source of a light emitting element (according to any of the embodiments herein) is turned on or off according to embodiments of the present disclosure. Specifically, Table 1 describes the various electrical components of the schematic diagram 950A when LEDs are turned on.

TABLE 1

| | LEDS ON |
|---|---|
| 1. | C1 stored high voltage |
| 2. | Reed switch enable with magnet |
| 3. | NMOS2 turns on, LEDs turn on |
| 4. | PMOS turns on |
| 5. | NMOS1 turns on |
| 6. | C1 discharged to low voltage |

The following Table 2 may describe engagement of various electrical components of the schematic diagram 950B when LEDs are turned off.

TABLE 2

| | LEDS OFF |
|---|---|
| 1. | C1 stored low voltage |
| 2. | Reed switch enable with magnet |
| 3. | NMOS2 turns off, LEDs turn off |
| 4. | PMOS turns off |
| 5. | NMOS1 turns off |
| 6. | C1 charged to high voltage (3 to 9 V battery) |

It should be understood that the schematic diagrams 950A and 950B may be used with any of the light emitting elements 102, 202, 302, 402, 502, 702, 802, 902 described herein.

Figure 14A:
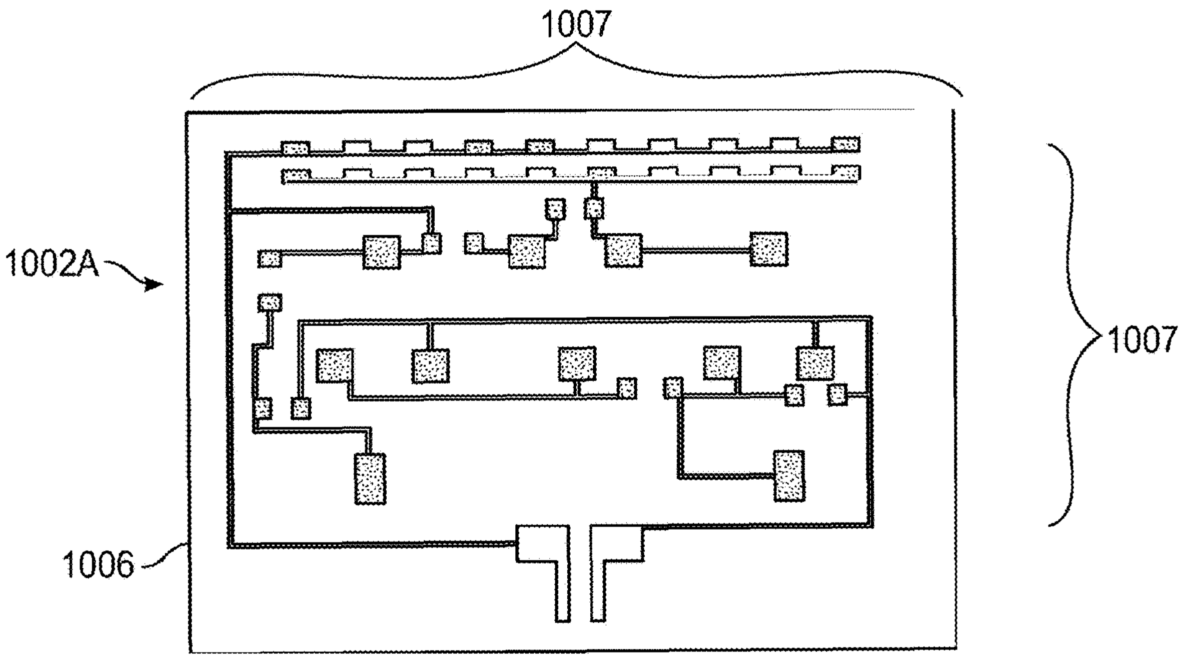
FIGS. 14A-14D illustrate one possible process flow for forming embodiments of the apparatus described herein, according to aspects of the present disclosure.

FIGS. 14A-14D illustrate one possible process flow of forming a light emitting element similar to the light emitting elements 102, 202, 302, 402, 502, 702, 802, 902 described herein. In FIG. 14A, a first configuration 1002A is shown, illustrating a substrate 1006 which may be formed with polyimide film and be flexible or deformable as described herein. As indicated, a plurality of electrical components 1007 may be soldered or otherwise formed along the substrate 1006. The electrical components 1007 may include the components described in FIG. 12A or FIGS. 13A-13B, although the present disclosure is not limited in this regard.

Figure 14B:
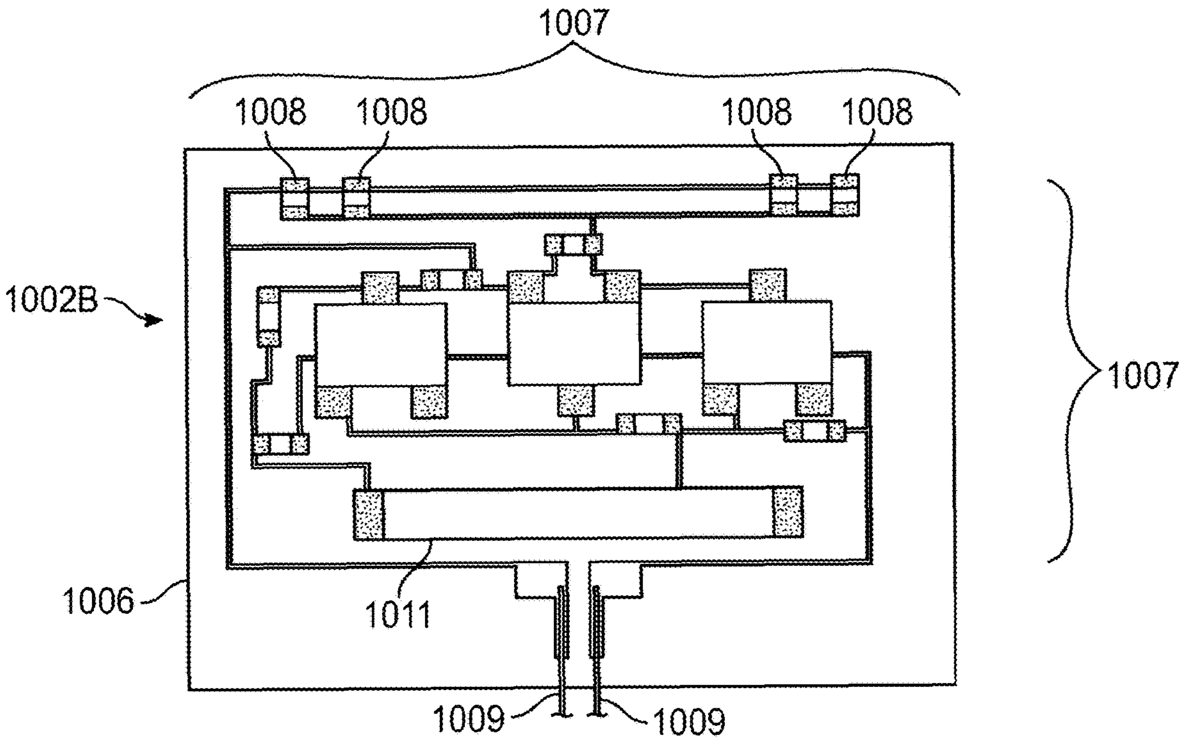

Referencing a second configuration 1002B shown in FIG. 14B, one or more SMD LEDs 1008 or other light sources may be mounted to the substrate 1006. Electrical wires 1009 may be electrically coupled to the SMD LEDs 1008 to form additional electrical connections as further described herein. In some embodiments, the SMD LEDs 1008 may be mounted to the substrate 1006, and the SMD LEDs 1008 may take the form of any of the embodiments of a light source as described herein. As further shown, a reed switch 1011 defined by the electrical components 1007 may be formed or mounted to the substrate 1006 and electrically coupled to the SMD LEDs 1008.

Figure 14C:
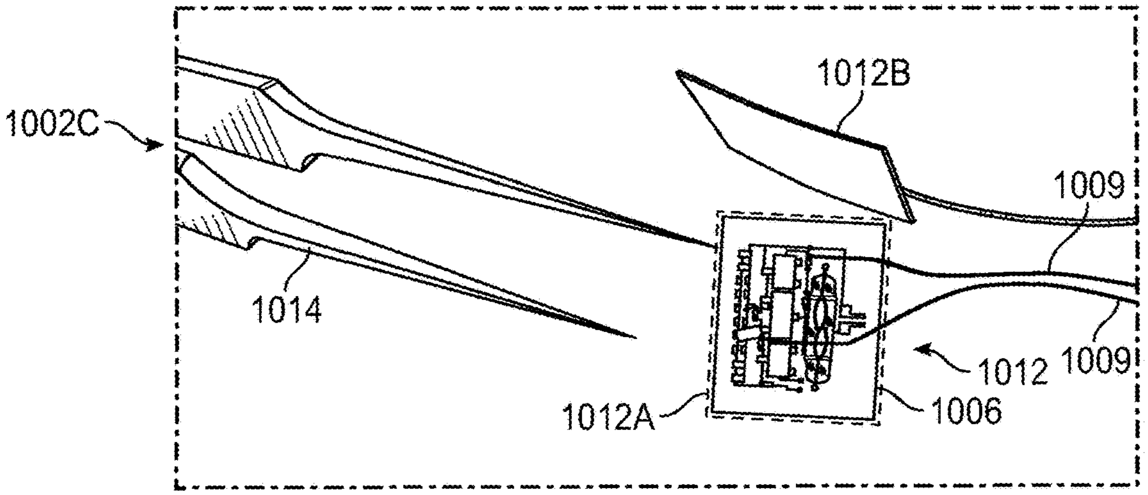

Referencing a third configuration 1002C shown in FIG. 14C, a surgical patty 1012 may be provided, and cut at least partially to define a first portion 1012A and a second portion 1012B of the patty 1012. Using forceps 1014 or other suitable tool, the substrate 1006 may be disposed along a surface of the first portion 1012A of the patty 1012 as indicated. In some embodiments, an adhesive (not shown) may be applied to maintain the substrate 1006 in a stationary position relative to the first portion 1012A of the patty 1012. As further shown, the electrical wires 1009 extend from the substrate 1006 and remain accessible for electrical connections.

Figure 14D:
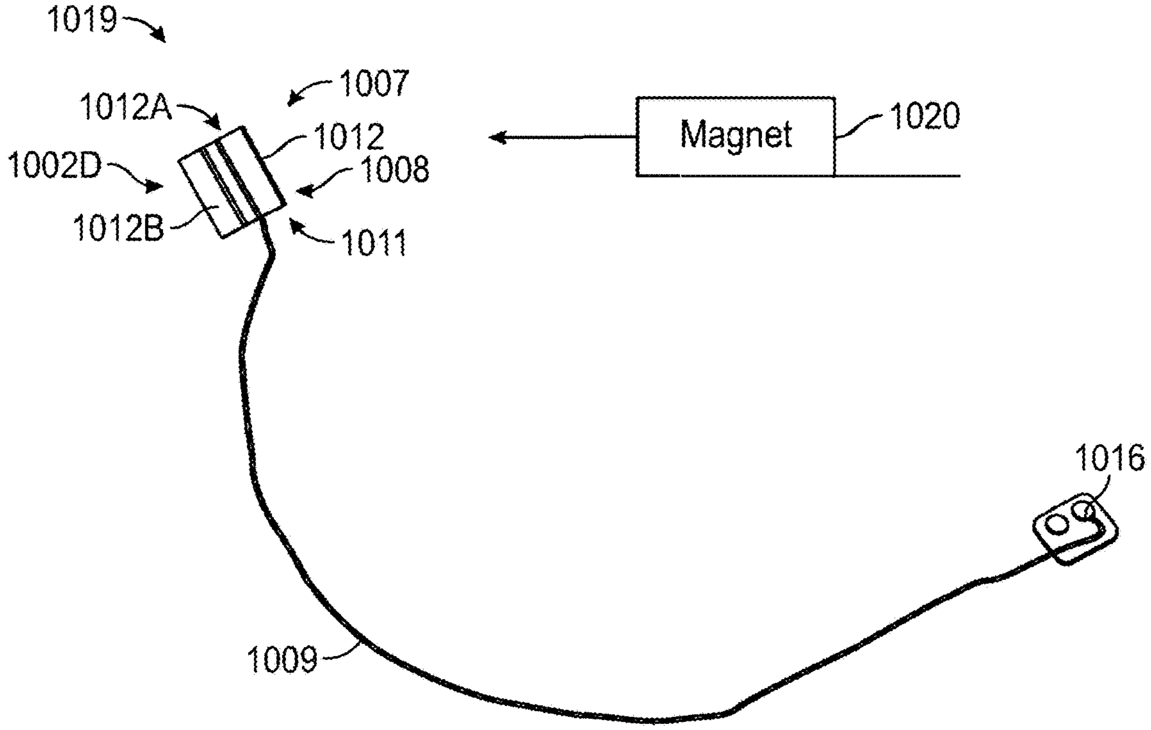

Referring a fourth configuration 1002D shown in FIG. 14D, the first portion 1012A and the second portion 1012B of the patty 1012 may be bonded together to encapsulate the substrate 1006 (including the SMD LEDs 1008) within the patty 1012 to form a light emitting element 1019 similar to the other light emitting elements described herein. In this manner, the patty 1012 provides an outer layer (similar to the embodiments of an outer layer described herein) such that the substrate 1006 is fully insulated from e.g., bodily fluids or other possible contaminants. It should be understood that the present disclosure is not limited to implementing a surgical patty as described with this embodiment and that the outer layer 110, 210, 310, 410, and 510 may be formed without a surgical patty. For example, the outer layer 110, 210, 310, 410, and 510 may be formed using deposition, sputtering, etching, chemical vapor deposition, or otherwise woven about the respective substrates and light sources. Alternatively, in other embodiments, a surgical patty may be implemented as one portion of the outer layer 110, 210, 310, 410, and 510.

As further indicated, the electrical wires 1009 may be connected to a power supply 1016 which may include a battery, USB connector, plug, or other suitable power source. During deployment, the SMD LEDs 1008 of the light emitting element 1019 may be engaged and illuminated by passing a magnet 1020 over the light emitting element 1019, thereby activating the reed switch 1011 defined among the electrical components 1007 to draw power from the power supply 1016. Other mechanisms for activating the SMD LEDs 1008 are contemplated and described above. In some embodiments, the light emitting element 1019 as assembled weighs approximately 0.8 grams.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An apparatus for surgical lighting of a surgical area, comprising:

an outer layer, the outer layer being biocompatible and the outer layer including a textile material configured to establish a barrier to fluids along a surgical area and provide a protective barrier for tissue; and a light source enclosed within the outer layer;

wherein the apparatus is configured for removeable placement in the surgical area;

wherein the outer layer comprises a memory-retaining metal, such that the outer layer is deformable or may be morphed to predetermined shape configurations and temporarily retains such configurations during deployment.

2. The apparatus of claim 1, wherein the apparatus is packaged in a folded configuration suitable for communication through a surgical port.

3. The apparatus of claim 1, wherein the light source comprises a light emitting diode tape, the light emitting diode tape being malleable and memory-retaining.

4. The apparatus of claim 1, further comprising:

a power supply connected to the light source.

5. The apparatus of claim 4, further comprising:

an actuating mechanism configured to activate the power supply for emitting light from the light source.

6. The apparatus of claim 5, further comprising:

an antennae connected to the power supply, the actuating mechanism configured to transmit a radio-frequency signal to the antennae to activate the power supply and emit the light from the light source.

7. The apparatus of claim 4, further comprising an insulated electrical conduit coupled between the light source and the power supply.

8. The apparatus of claim 1, wherein the light source emits the light at a predefined wavelength corresponding to a predefined surgical function.

9. The apparatus of claim 1, further comprising:

a substrate enclosed within the outer layer, the substrate being malleable and having the light source mounted thereon.

10. The apparatus of claim 9, wherein the substrate includes a flexible printed circuit board.

11. The apparatus of claim 1, further comprising a retrieval tether coupled to the outer layer configured for removing the apparatus from a surgical area.

12. A method of forming an apparatus for surgical lighting of a surgical area, comprising:

providing a light source, the light source configured to illuminate a surgical area; and encapsulating the light source within an outer layer, the outer layer being biocompatible and the outer layer including a textile material configured to establish a barrier to fluids along a surgical area and provide a protective barrier for tissue;

wherein the apparatus is configured for removeable placement in the surgical area;

wherein the outer layer comprises a memory-retaining metal, such that the outer layer is deformable or may be morphed to predetermined shape configurations and temporarily retains such configurations during deployment.

13. The method of claim 12, further comprising:

folding the apparatus into a folded configuration suitable for communication through a surgical port.

14. The method of claim 12, further comprising:

connecting the light source to a power supply.

15. The method of claim 14, wherein the power supply is encapsulated within the outer layer and positioned adjacent the light source.

16. An apparatus for surgical lighting of a surgical area, comprising:

an outer layer, the outer layer being biocompatible and the outer layer including a textile material configured to establish a barrier to fluids along a surgical area and provide a protective barrier for tissue;

a substrate enclosed within the outer layer, the substrate being oriented in a generally central position along a body of the apparatus;

a light source mounted to the substrate and enclosed within the outer layer;

wherein the apparatus is configured for removeable placement in the surgical area;

wherein the outer layer comprises a memory-retaining metal; and wherein the outer layer includes one or more layers including non-absorptive fibers woven near borders of the outer layer to form a uniform surface and to enclose the substrate and the light source within the generally central position along the body of the apparatus.

* * * * *